United States Patent
Parodi

(10) Patent No.: US 6,824,558 B2
(45) Date of Patent: *Nov. 30, 2004

(54) ENDOLUMINAL DEVICE AND METHOD FOR TREATING BRANCHED LUMEN HAVING A RESTRICTED SECTION

(75) Inventor: Juan Carlos Parodi, Capital Federal (AR)

(73) Assignee: Boston Scientific Corporation, Natick, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 09/764,554

(22) Filed: Jan. 18, 2001

(65) Prior Publication Data

US 2001/0002443 A1 May 31, 2001

Related U.S. Application Data

(63) Continuation of application No. 09/139,957, filed on Aug. 25, 1998, now Pat. No. 6,238,432.

(51) Int. Cl.$^7$ .................................................. A61F 2/06
(52) U.S. Cl. ...................... 623/1.13; 623/1.35; 623/1.3; 623/1.31
(58) Field of Search ............................... 623/1.13, 1.27, 623/1.3, 1.31, 1.35, 1.37, 1.1

(56) References Cited

U.S. PATENT DOCUMENTS

| | | | |
|---|---|---|---|
| 5,064,435 A | | 11/1991 | Porter |
| 5,405,378 A | * | 4/1995 | Strecket ......................... 623/1 |
| 5,476,506 A | * | 12/1995 | Lunn ............................. 623/1 |
| 5,575,817 A | | 11/1996 | Martin |
| 5,693,088 A | | 12/1997 | Lazarus |
| 5,741,325 A | * | 4/1998 | Chaikof et al. ................ 623/1 |
| 5,755,770 A | | 5/1998 | Ravenscroft |
| 5,755,779 A | * | 5/1998 | Horiguchi ...................... 623/1 |
| 5,800,514 A | | 9/1998 | Nuñez et al. |
| 5,824,040 A | | 10/1998 | Cox et al. |
| 5,824,042 A | * | 10/1998 | Lombardi et al. ............. 623/1 |
| 5,827,320 A | | 10/1998 | Richter et al. |
| 5,843,158 A | | 12/1998 | Lenker et al. |
| 5,922,019 A | | 7/1999 | Hankh et al. |
| 6,129,756 A | * | 10/2000 | Kugler et al. ............... 623/1.27 |
| 6,149,682 A | * | 11/2000 | Frid ............................ 623/1.35 |
| 6,179,858 B1 | * | 1/2001 | Squire et al. ................ 606/198 |
| 6,273,909 B1 | * | 8/2001 | Kugler et al. ............... 623/1.13 |
| 6,306,164 B1 | * | 10/2001 | Kujawski ..................... 623/1.35 |

FOREIGN PATENT DOCUMENTS

| | | |
|---|---|---|
| FR | 2 756 173 | 5/1998 |
| WO | 97/17910 | 5/1997 |
| WO | 98/27895 | 7/1998 |

OTHER PUBLICATIONS

US application 09/753,119, pub. No. US 2002/0052643, Wholey et al., Tapered Endovascular Stent Graft and Method of Treating Abdominal Aortic Aneurysms and Distal Iliac Aneurysms.*

* cited by examiner

Primary Examiner—Bruce Snow
Assistant Examiner—Cheryl Miller
(74) Attorney, Agent, or Firm—RatnerPrestia

(57) ABSTRACT

A stent graft device has an upper main tubular portion dividing into two tubular limbs and is adapted for location in an aorta having an aneurysm. The stent graft device is well suited for an aorta having a restricted section having an inner diameter smaller than the sum of the inner diameters of the iliac arteries, which branch from the aorta. The diameters of the two tubular limbs are sufficiently small to allow for both tubular limbs to be deployed side-by-side in a fully expanded state within the restricted section without being constrained by the aorta inner surface. The limbs also have distal end portions having diameters larger than the diameters of limbs at the area near the restricted section for being retained within the iliac arteries.

10 Claims, 1 Drawing Sheet

ENDOLUMINAL DEVICE AND METHOD FOR TREATING BRANCHED LUMEN HAVING A RESTRICTED SECTION

This application is a continuation of U.S. patent application Ser. No. 09/139,957, filed Aug. 25, 1998 now U.S. Pat. No. 6,238,432.

BACKGROUND OF THE INVENTION

1. Field of the Invention

The present invention relates to the field of percutaneous transluminal treatment of blood vessels aneurysms and, particularly refers to a modular graft device for treatment of an aorta aneurysm by replacement or encasement of the affected aorta wall with the inventive graft device.

2. Description of the Prior Art

As it is well known in the art, an aneurysm is a widening or dilation of a blood vessel, artery or vein, caused by thinning of the vessel wall. The rupture of the vessel wall is a lethal complication as long as it results in massive hemorrhage. Aneurysms usually occur in arteries but may also be seen in the heart after local damage, or in veins.

Arterial aneurysms are more common than venous and they may be caused by congenital thinning of the muscular portions of the artery, during atherosclerotic degeneration of the aorta or of the carotid or basilar arteries, by trauma to a vessel wall, by infectious injury, or by degeneration from other causes. The likelihood of rupture is increased by high blood pressure.

An aneurysm in the largest artery in the human body, the aorta, will therefore result in a very important situation. The aorta is the primary vessel carrying blood from the heart to the rest of the circulatory system. The aorta arises from the base of the left ventricle of the heart and arches over and backward to the left front side of the vertebral column, or spine. Then, it passes downward along the spine and divides into the common iliac arteries, which supply blood to the extremities.

For descriptive purposes, the aorta is usually divided into the ascending aorta, the aortic arch, the thoracic descending aorta, and the abdominal aorta. The renal arteries, mesenteric arteries, and many other branches arise from the abdominal aorta.

The walls of the aorta are quite thick and consist primarily of strong, elastic connective tissue. The distensibility of the aorta and its major branches is such that this central reservoir acts as a second heart pump.

A widely used technique for treating a patient harboring an aneurysm is the percutaneous transluminal angioplasty, generally used in the treatment of coronary heart diseases, which technique involves the widening of the arteries that have been dangerously narrowed under the effects of the atherosclerosis, that is, by the buildup of deposits called plaque on their interior walls. A flexible tube, or catheter, is first inserted through a skin incision into an artery. The catheter is manipulated transluminally until it reaches the constriction site. A small balloon at the end of the catheter is then inflated, compressing the plaque and widening the passage. Although this procedure has been largely used since the 1970s, the PTA has been generally restricted to some vessels, coronary arteries, for example, but the use of balloons has not been entirely successful in larger vessels like the aorta because of, among other things, the strong calcification of the plaques.

In addition to the foregoing, with a ruptured aneurysm, a person may be treated with reduction of blood pressure and replacement of the weakened vessel by a graft or encasement in plastic, or mechanically stopping blood flow to or through the aneurysm.

The use of graft devices has been found successful in the treatment of abdominal aorta aneurysms where a graft device comprising an upper main portion and two pending limbs is inserted into the aorta with the main portion retained in the proximal end of the aorta and respective distal ends of the limbs are inserted and retained into the respective iliac arteries, thus replacing the aorta walls by the graft. However, the aortic aneurysms are very often heavily calcified and strongly narrowed by the atherosclerotic plaques. Under these circumstances, and perhaps due to a side effect, the diameter of the iliac arteries tend to dilate with the result that, frequently, the diameter of the aorta, in the zone harboring the aneurysm, that is the distal aorta, is smaller than the sum of the diameters of both iliac arteries. In practice, for example, if the distal aortic diameter is 20 mm and the iliac artery diameter exceeds 11 mm, a 12 mm iliac graft device is necessary to have the distal ends of the graft limbs inserted and retained into the respective iliac arteries. Thus, each graft limb must have a diameter of 12 mm, the graft limbs being extending into and along the distal aortic aneurysm of 20 mm, which, in addition, as stated above, is heavily calcified and rigid. Therefore, the graft limbs with 24 mm (12 mm+12 mm) will be constrained under the restricted section of the aneurysm. More particularly, the exceeding 4 mm in the diameter will be compressed by the aneurysm. While the graft construction and the materials used in its manufacture make the graft device to be flexible enough to be located into the distal aorta, through the restricted section thereof, angulation and compression of the graft limbs could be responsible for the occurrence of limb occlusion and the resulting ischemia of the limbs.

In view of the foregoing it would be desirable to have a graft device capable of being easily inserted and located into a distal aorta with aneurysm, but capable also of being accommodated in the restricted section without being impaired by the smaller diameter available at the restricted section of the aorta.

3. Summary of the Invention

It is therefore one object of the present invention to provide a stent graft device for location within an aorta having an inner diameter and its bifurcation into iliac arteries each having an inner diameter, the aorta inner diameter being smaller than a sum of the iliac inner diameters. The graft comprises a proximal main tubular portion to be retained within an upper portion of the aorta, the proximal main tubular portion having a first diameter and being divided into two tubular limbs, each limb having a second diameter and a distal end portion to be located inside an associated iliac artery and to be held against an inner surface of the iliac artery. The distal end portion defines a third diameter larger than the second diameter, the second diameter being of an effective size such that the two tubular limbs can be accommodated within the aorta inner diameter without restriction. The stent graft device may be unitary, which means that the device comprises a single-piece, non-modular construction.

It is still another object of the present invention to provide a stent graft device of the type to be located within an aorta and its bifurcation into iliac arteries, the graft comprising a proximal main tubular portion to be retained within an upper portion of the aorta, the proximal main tubular portion having a first diameter and dividing into two tubular limbs each limb having a second diameter and a distal end portion to be located inside an associated iliac artery and held against an inner surface of the iliac artery, the distal end portion defining a third diameter larger than the second diameter, the distal end portion being merged with the associated graft limb through a transition flared portion.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
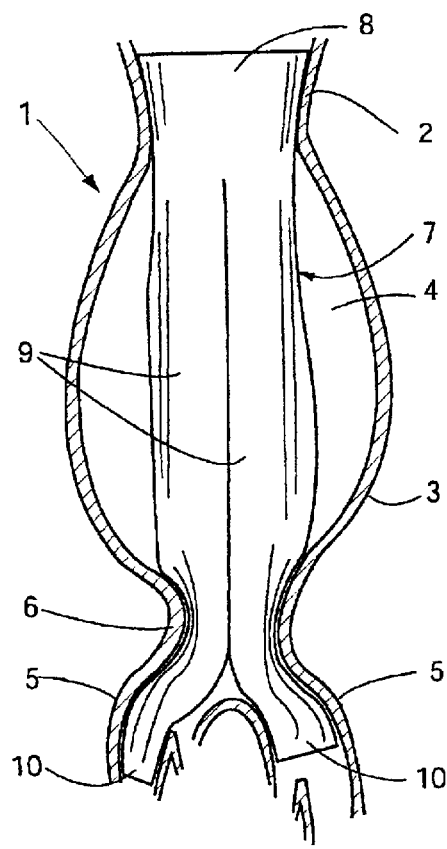
FIG. 1 shows a partial cross-sectional view of an abdominal aorta affected by an aneurysm and including a graft device of the prior art.

Now referring in detail to the drawings it may be seen from FIG. 1 that an abdominal aorta 1 comprises an upper proximal portion 2, a distal portion 3 affected by an aneurysm 4, the aorta dividing, at the lower part thereof, into two iliac arteries 5, with a restricted section being formed at 6. To treat the affected patient, a known graft device 7 is inserted and retained into the aorta, the graft having a proximal main tubular portion 8 to be retained, by any known technique in the art, within upper portion 2 of the aorta. Portion 8 divides into two tubular limbs 9, pending from portion 8 and each limb 9 ends in a distal end 10 capable of being retained within the iliac arteries and against inner surfaces of these arteries.

As it is clear from the drawing, the restriction 6 constrains the two limbs 9 of graft 7 causing a limb occlusion and ischemia of the limb. To overcome this drawback of the prior art, the inventor has developed a new graft device as shown in FIG. 2.

Figure 2:
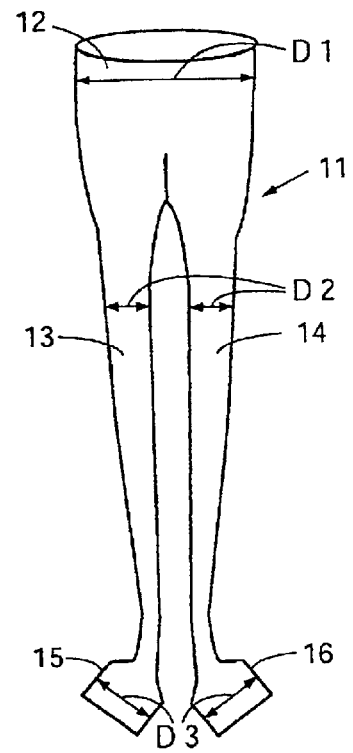
FIG. 2 shows a perspective elevation view of an stent graft device devised according to the present invention.
Figure 3:
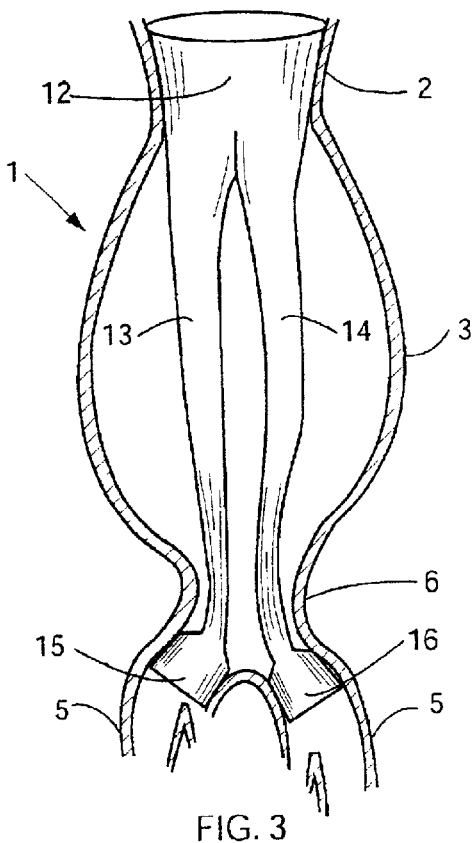
FIG. 3 shows a partial cross-sectional view of an abdominal aorta, similar to FIG. 1, but treated with the graft device of FIG. 2, according to the invention.

According to the invention, the graft device 11, shown in FIGS. 2 and 3, has a proximal main tubular portion 12 with a first diameter D1. Portion 12 divides into two tubular limbs 13, 14, pending from portion 12, each limb 13, 14 defining a second diameter D2 and ending in an enlarged distal end portion 15, 16, respectively, capable of being located and firmly retained inside an associated iliac artery 5, so as to be held against an inner surface of the iliac artery. Each portion 15, 16 defines a third diameter D3 at a larger, preferably cylindrical tubular wall thereof.

Diameter D1 generally is determined by the size and available section at portion 2 of aorta 1, as well as from the aneurysm size. The same occurs with diameters D2, D3, which are also determined based on the iliac sizes and aneurysm restriction. The graft, however, is manufactured in a limited plurality of sizes which must be accommodated to the aorta under treatment, without the different diameters being capable of being varied in a graft. To facilitate accommodation of the graft inside the aorta and to avoid the constraining situation at restriction 6, diameter D2, according to the invention, is reduced as compared to the diameters used in the prior art grafts while a new distal end portion 15, 16 is added at the end of the limbs to define a diameter D3 which is larger than diameter D2. Generally speaking, the shape of portion 15, 16 may be called as having an "Elephant Foot" appearance, with the transition between the limb diameter D2 to end portion diameter D3 being shaped in any generic flared configuration.

Figure 4:
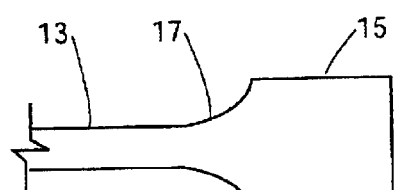
FIG. 4 shows a side view of a distal end portion of a graft limb according to the invention, with a flared transition portion merging the limb to the distal end portion.
Figure 5:
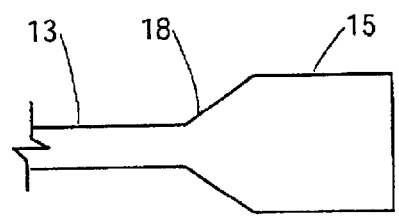
FIG. 5 shows a side view, similar to FIG. 4, of a distal end portion according to another embodiment of the invention, with a conical transition portion being illustrated between the limb and the distal end portion.

As it is shown in FIG. 4, a first embodiment shows that the transition or merging between a limb 13 and its distal end portion 15 may be devised through a curved trumpet-shaped transition portion 17. FIG. 5 shows another embodiment where the transition portion is a conical portion 18. In any case, distal end portion 15, 16 may be cylindrical or may have any shape provided that the end portion is sized and configured to be efficiently retained into the corresponding iliac artery, as shown in FIG. 3. The material from which the graft device of the invention may be manufactured may be the same used for the graft devices of the prior art.

While preferred embodiments of the present invention have been illustrated and described, it will be obvious to those skilled in the art that various changes and modifications may be made therein without departing from the scope of the invention as defined in the appended claims.

I claim:

1. An endoluminal device sized to be deployed within a first lumen comprising a restricted section having an inner surface with an inner diameter and a bifurcation into branch lumens each having an inner surface with an inner diameter, the restricted section inner diameter being smaller than a sum of the branch lumen inner diameters, the device comprising a proximal main tubular portion to be retained within a proximal portion of the first lumen and having a first diameter and two tubular limbs depending from the proximal main tubular portion, each limb having a second diameter and a distal end portion for deployment inside one of the branch lumens against the branch lumen inner surface, the distal end portion defining a third diameter larger than the second diameter, wherein the sum of the two second diameters is sized to be less than the restricted section inner diameter and each tubular limb comprises a trumpet-shaped, concave transition portion having a curved slope extending from the second diameter to the third diameter when viewed in longitudinal section in a non-deployed configuration, the end portion having a defined length comprising the third diameter.

2. The endoluminal device of claim 1, wherein the distal end portion is cylindrical.

3. The endoluminal device of claim 1, wherein the second diameter is sized to be smaller than the branch lumen inner surface diameter and the third diameter, in an unconfined state, is sized to be larger than the branch lumen inner surface diameter.

4. The endoluminal device of claim 1, wherein the device is unitary.

5. The endoluminal device of claim 1 wherein the device has a fully expanded configuration and a compressed configuration and the distal end portion third diameter is constrained from reaching the fully expanded configuration by the branch lumen inner surface and the second diameters of the two tubular limbs are sufficiently small to allow both tubular limbs to be deployed side-by-side in their fully expanded configuration within the first lumen restricted section without being constrained by the restricted section inner surface.

6. The device of claim 1, wherein a sum of the third diameters in a deployed configuration is at least 20% greater than a sum of the second diameters in a deployed configuration.

7. An endoluminal device sized to be deployed within a first lumen having a restricted section with a diameter and a bifurcation into a plurality of branch lumen each having an inner diameter, the device comprising:

a proximal main tubular portion to be retained within a proximal portion of the first lumen; and a first and a second tubular limb depending from said proximal main tubular portion;

wherein each of said first and second tubular limbs comprises: (i) an elongated portion for extending across the restricted section and having a first diameter which is sized to be less than one-half of the restricted diameter; (ii) a distal end portion to be located inside an associated branch lumen and to be held against an inner surface of the branch lumen, the distal end portion defining a second diameter larger than the first diameter and sized to be greater than one-half of the restricted diameter, the distal end portion having a defined length comprising the second diameter; and (iii) a trumpet-shaped, concave transition portion extending between the elongated portion and the distal end portion having a curved slope when viewed in longitudinal section in a non-deployed configuration.

8. The device of claim 7, wherein a sum of the second diameters in a deployed configuration is at least 20% greater than a sum of the first diameters in a deployed configuration.

9. A method of treating an afflicted portion of a branched lumen, the method comprising the steps of:

identifying a first lumen comprising a restricted section having an inner surface with an inner surface diameter and a bifurcation into branch lumen each having an inner surface with an inner surface diameter, the first lumen restricted section inner surface diameter being smaller than the sum of the branch lumen inner surface diameters, implanting an endoluminal device in a location in the first lumen, the endoluminal device comprising a proximal main tubular portion having a first diameter and two tubular limbs depending from the main tubular portion, each limb having a second diameter and a distal end portion, the distal end portion having a third diameter larger than the second diameter the location comprising a location in which: (i) said proximal main tubular portion is disposed within a proximal portion of the first lumen; (ii) each of said tubular limbs is disposed inside an associated branch lumen; and (iii) the distal end portion is disposed within one of said branch lumen and restricted from full expansion by the branch lumen inner surface, wherein the second diameters of each of said two tubular limbs are sufficiently small to allow both tubular limbs to be deployed side-by-side in a fully expanded state within the restricted section inner diameter without being constrained by the restricted section inner surface and wherein each tubular limb comprises a trumpet-shaped, concave transition portion extending from the second diameter to the third diameter having a curved slope when viewed in longitudinal section in a non-deployed configuration, the end portion having a defined length comprising the third diameter.

10. The method of claim 9, wherein the step of identifying the first lumen comprises identifying a lumen in which the sum of the branch lumen inner surface diameters is 20% greater than the restricted section inner surface diameter.

* * * * *